United States Patent [19]

Moser et al.

[11] Patent Number: 5,002,606

[45] Date of Patent: Mar. 26, 1991

[54] OPTICALLY ACTIVE N-(1'-METHYL-2'-METHOXYETHYL)-N-CHLOROACETYL-2-ETHYL-6-METHYLANILINE AS HERBICIDE

[75] Inventors: Hans Moser, Magden; Christian Vogel, Binningen, both of Switzerland

[73] Assignee: Ciba-Geigy Corporation, Ardsley, N.Y.

[21] Appl. No.: 679,439

[22] Filed: Dec. 7, 1984

Related U.S. Application Data

[63] Continuation-in-part of Ser. No. 434,432, Oct. 14, 1982, abandoned.

[30] Foreign Application Priority Data

Oct. 16, 1981 [CH] Switzerland ............... 6624/81

[51] Int. Cl.$^5$ ................. A01N 37/22; C07C 233/25
[52] U.S. Cl. ..................... 71/118; 564/214; 564/304
[58] Field of Search ............ 564/214, 304; 71/118

[56] References Cited

U.S. PATENT DOCUMENTS

| | | | |
|---|---|---|---|
| 3,028,430 | 4/1962 | Gillingham | 564/304 X |
| 3,576,854 | 4/1971 | Felder et al. | 564/304 X |
| 3,937,730 | 2/1976 | Vogel et al. | 564/214 |
| 3,969,397 | 7/1976 | Kaiser et al. | 564/304 X |

OTHER PUBLICATIONS

Fieser et al., "Reagents for Organic Synthesis", vol. 6, p. 64 (1977).

Burger, "Medicinal Chemistry", Part I, 3rd Ed., pp. 81–82 and 100–103 (1970).

Wagner et al., "Synthetic Organic Chemistry", pp. 155–156 (1963).

Hans Moser et al., Der Einfluβ von Atropisomerie und chiralem Zentrum auf die biologische Aktivität des Metolachlor, pp. 451–462 (1976).

Chem. Abstr. 97-7167h, vol. 97, pp. 569 (1982).

*Primary Examiner*—Richard L. Raymond
*Attorney, Agent, or Firm*—Kevin T. Mansfield; Edward McC. Roberts

[57] ABSTRACT

The optically active mixture of isomers of aRS,1'S(−)-N-(1'-methyl-2'-methoxyethyl)-N-chloroacetyl-2-ethyl-6-methylaniline has improved action against problem weeds over the racemic mixture of isomers known as "Metolachlor".

6 Claims, No Drawings

OPTICALLY ACTIVE N-(1'-METHYL-2'-METHOXYETHYL)-N-CHLOROACETYL-2-ETHYL-6-METHYLANILINE AS HERBICIDE

DETAILED DISCLOSURE

The present invention relates to a mixture of diastereoisomers of N-(1'-methyl-2'-methoxyethyl)-N-chloroacetyl-2-ethyl-6-methylaniline having aR,1'S(−) and aS,1'S(−) configuration, to a process for the preparation thereof, to herbicidal compositions which contain this mixture as active ingredient, and to the use of said mixture for controlling weeds.

N-(1'-Methyl-2'-methoxyethyl)-N-chloroacetyl-2-ethyl-6-methylaniline is already known as a mixture of its diastereoisomers. This mixture of diastereoisomers, its preparation and the use thereof as plant regulator and herbicide is described e.g. in U.S. Pat. No. 3 937 730. It is known by the trivial name Metolachlor.

Two elements of asymmetry are present in the molecule of N-(1'-methyl)-2'-methoxyethyl)-N-chloroacetyl-2-ethyl-6-methylaniline of the formula I:

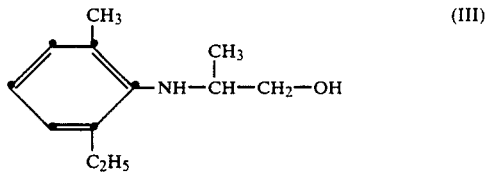

One of them, a chiral center, is located at the carbon atom C 1' in the 1'-methyl-2'-methoxyethyl group and the other, a chiral axis, is formed by the obstruction to the free rotation about the bond a between the nitrogen atom and phenyl radical. In accordance with the presence of two elements of asymmetry, N-(1'-methyl-2'-methoxyethyl)-N-chloroacetyl-2-ethyl-6-methylaniline is obtained, when prepared by the methods known up to now, as a mixture of 4 diastereoisomers having respectively the configuration aR,1'R(−), aS,1'S(+), aR,1'S(−) and aS,1'R(+). Up to now, nothing is known about the biological activity of the individual diastereoisomers.

It has been found that a mixture of diastereoisomers of N-(1'-methyl-2'-methoxyethyl)-N-chloroacetyl-2-ethyl-6-methylaniline having aR,1'S and aS,1'S configuration has a substantially better herbicidal action than the previously known mixture of diastereoisomers which contains all possible diastereoisomeric forms.

Accordingly, the present invention relates to a mixture of the diastereoisomers of N-(1'-methyl-2'-methoxyethyl)-N-chloroacetyl-2-ethyl-6-methylaniline having negative rotation and aR,1'S and aS,1'S configuration. The mixture of diastereoisomers of this invention will be referred to throughout this specification as aRS,1'S(−)-N-(1'-methyl-2'-methoxyethyl)-N-chloroacetyl-2-ethyl-6-methylan iline.

The mixture of the diastereoisomers of N-(1'-methyl-2'-methoxyethyl-N-chloroacetyl-2-ethyl-6-methylaniline having aR,1'S and aS,1'S configuration can be prepared by a process, which comprises reducing S(−)-N-(2-ethyl-6-methylphenyl)-alanine of the formula II:

to 1'S(−)-N-(1'-methyl-2'-hydroxyethyl)-2-ethyl-6-methylaniline of the formula III:

chloroacetylating the compound of formula (III) at the nitrogen and subsequently etherifying the resultant aRS,1'S(+)-N-(1'-methyl-2'-hydroxyethyl)-N-chloroacetyl-2-ethyl-6-methylaniline of the formula IV:

in the presence of a strong acid, with methanol, at the 2'-hydroxy group.

The starting S(−)-N-(2-ethyl-6-methylphenyl)alanine may be obtained by converting racemic N-(2-ethyl-6-methylphenyl)alanine, in a suitable solvent, with an optically active base into diastereomeric salts, separating said diastereomeric salts by fractional crystallisation and then cleaving them.

The racemic N-(2-ethyl-6-methylphenyl)-alanine may itself be obtained by reacting 2-ethyl-6-methylaniline, in the presence of a base, with a 2-halopropionic acid ester and subsequently saponifying the reaction product.

Suitable solvents are diisopropyl ether, ethyl acetate, acetonitrile and water.

Examples of suitable optically active bases are:
S(+)-2-amino-1-butanol, R(−)-2-amino-1-butanol, L-(+)-threo-2-aminophenyl-1,3-propanediol, (−)-brucine,
(+)-quinidine, (−)-quinine, (−)-cinchonidine, (+)-cinchonine,
(+)-dehydroabietylamine, (+)-yohimbine, (−)-nicotine,
(−)-ephedrine, (+)-ephedrine, (−)-N-methylephedrine,
R(+)-1-phenylethylamine, S(−)-1-phenylethylamine,
(+)-pseudoephedrine and (−)-α-phenyl-β-p-tolylethylamine.

Among the above mentioned optically active bases, R(+)-1-phenylethylamine is particularly preferred.

The reduction of S(−)-N-(2-ethyl-6-methylphenyl)-alanine of the formula II to 1'S(−)-N-(1'-methyl-2'-hydroxyethyl)2'-ethyl-6-methylaniline of the formula III is conveniently carried out in an inert solvent. Examples of suitable inert solvents are aliphatic and aromatic hydrocarbons and, in particular, ethers. Specific examples of suitable solvents are hexane, cyclohexane, benzene, toluene, diethyl ether, tetrahydrofuran and dioxan.

Suitable reducing agents are lithium aluminium hydride and, in particular, borane. It is preferred to use borane in the form of a complex, especially as borane-dimethyl sulfide complex or as borane-tetrahydrofuran complex. The reducing agent is normally employed in stoichiometric amount up to an excess of 100%, based on the stoichiometric amount. The reaction temperature may be between 10° C. and the boiling point of the reaction mixture.

The conversion of 1'S(−)-N-(1'-methyl-2'-hydroxyethyl)-2ethyl-6-methylaniline of the formula II into aRS,1'S(+)-N-(1'-methyl-2-hydroxyethyl)-N-chloroacetyl-2ethyl-6-methylaniline of the formula IV is carried out by reaction with a chloroacetylating agent such as chloroacetyl chloride or chloroacetic anhydride, in the presence of a base, in an inert solvent. Suitable bases are in particular alkali metal carbonates and bicarbonates, as well as tertiary amines such as triethylamine and pyridine. Suitable inert solvents are hydrocarbons such as hexane, cyclohexane, benzene, toluene and chlorobenzene. The chloroacetylating agent may be used in stoichiometric amount or in a small excess. In practice, molar ratios of S(−)-N-(1'-methyl-2'hydroxyethyl)-2-ethyl-6-methylaniline of the formula III to chloroacetylating agent of 1:1 to 1:1.1 have proved suitable. The reaction is carried out with cooling or at moderately elevated temperature. The temperature range from 0° C. to 50°0 C. has proved particularly suitable.

The etherification of the 2'-hydroxy group of the aRS,1'S(+)-N-(1'-methyl-2'-hydroxyethyl)-N-chloroacetyl-2-ethyl-6-methylaniline of the formula IV may be advantageously be carried out by heating the substance, in the presence of a strong acid, in absolute methanol at reflux temperature. Suitable strong acids for the reaction are in particular sulfuric acid and p-toluenesulfonic acid, which may be used in an amount of 0.1 to 0.3 mole per mole of aRS,1'S(+)-N-(1'-methyl-2'-hydroxyethyl)-N-chloroacetyl-2-ethyl-6-methylaniline of the formula IV The etherification may conveniently be carried out in the presence of a hydrophilic agent, especially a ketal such as 2,2-dimethoxypropane. An equimolar amount or an excess of the hydrophilic agent is employed.

The aRS,1'S(−)-N-(1'-methyl-2'-methoxyethyl)-N-chloroacetyl-2-ethyl-6-methylaniline obtainable by the process of this invention has an optical purity of 98% according to ¹H-NMR spectroscopy. Compared with the known mixture of diastereoisomers of N-(1'-methyl-2'-methoxyethyl)-N-chloroacetyl-2-ethyl-6-methylaniline, it has a markedly superior herbicidal action against weeds while not having increased phytotoxicity towards cultivated plants. It may therefore be formulated in known manner to herbicidal compositions and used for controlling weeds in cultivated plants.

In this description, the absolute configuration has been named in accordance with "Experientia", Vol. 12. pp. 81–94 (1956).

The invention also relates to herbicidal compositions which contain the active diastereoisomer of the formula I, as well as to methods of controlling weeds pre- and postemergence.

The compositions of this invention may be formulated in conventional manner and are prepared in a manner known per se by mixing and grinding optically active compounds of the formula I with suitable carriers, with or without the addition of dispersants and solvents. In this manner, dusts, tracking agents, granular formulations, wettable powders, pastes, emulsions, emulsifiable concentrates or solutions are prepared by known methods.

The rates of application for controlling weeds are normally from 0.1 to 10 kg of active ingredient per hectare, preferably 0.25 to 5 kg/ha.

Compared with the known mixture of isomers, the aRS,1'S(−) isomer of N-(1'-methyl-2'-methoxyethyl)-N-chloroacetyl-2-ethyl-6-methylaniline of this invention better tolerated by maize and soybeans. At the same time increased activity against the following species of weeds has been observed: Avena fatua (wild oats), *Alopecurus myosuriodes, Cyperus esculantus, Amaranthus retroflexus, Galium aparine*, pastinaca sativa, *Rumex obt.* and *Solanum nigrum*. Surprising, and of great importance, is the good action against *Cyperus esculentus*. This ubiquitous weed is resistant to most herbicides and is therefore at present counted among the problem weeds. Cyperus esculentus can be controlled in crops of useful plants with aRS,1'S-(−)-N-(1'-methyl-2'-methoxyethyl)-N-chloroacetyl-2-ethyl-6-methylaniline at exceedingly low rates of application. At the same time, a stimulation of the root growth of germinating plants is observed.

The following Examples illustrate in more detail the preparation and the use of the mixture of diasteroisomers of N-(1'-methyl-2'-methoxyethyl)-N-chloroacetyl-2-ethyl-6-methylaniline having aR,1'S and aS,1'S configuration. Parts and percentages are by weight.

EXAMPLE 1

Preparation of racemic N-(2-ethyl-6-methyl-phenyl)-alanine

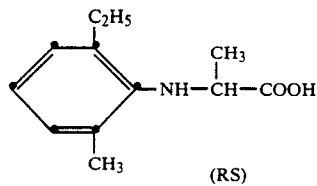

(RS)

(a) N-(2-Ethyl-6-methylphenyl)-alanine methyl ester

A 4.51 ml sulfonating flask is charged with 836 ml (6 moles) of 2-ethyl-6-methylaniline, 554 g (6.6 moles) of NaHCO₃ and 2007 ml (18 moles) of methyl 2-bromopropionate. The mixture is stirred and slowly heated for 1 hour to 120–125° C. bath temperature while introducing nitrogen. Stirring of the dark reaction mixture is continued for 18 hours at this temperature accompanied by evolution of CO₂. After it has cooled, the reaction mixture is poured into 3 liters of ice-water and extracted portionwise with ethyl acetate. The ethyl acetate fractions are dried over sodium sulfate and concentrated in a rotary evaporator at 40° C. Excess methyl 2-bromopropionate is stripped off in vacuo and the residue is subjected to fractional distillation over a metal-coated 60 cm Vigreux column, affording 1108 g of ester with a boiling point of 141°–143° C. (12 mbar).

(b) N-(2-Ethyl-6-methylphenyl)-alanine 1015 g (4.58 moles) of the above ester and 31 ml of 2N sodium hydroxide solution are stirred at room temperature. After 6 hours the emulsion has become a solution in which no more starting material is present (analysis by gas chromatography). While stirring and cooling with ice, the alkaline solution is adjusted to pH 4 with concentrated sulfuric acid. The acid precipitates in the form of an oil, which crystallises after prolonged stirring. Solid sodium chloride is added until saturation is reached, then the precipitate is isolated by filtration and washed with ice-water. The filter cake is taken up in ethyl acetate, the water is removed, and the organic phase is dried over sodium sulfate. The ethyl acetate is removed by distillation, affording the racemic acid 1 in the form of a brown oil which is crystallised from n-hexane with the addition of cyclohexane. Yield: 771 g with a melting point of 66° 14 70° C.

(c) Cleaving racemic N-(2-ethyl-6-methylphenyl)-alanine with R(+)-phenylethylamine 222 ml (1.7 moles) of R(+)-1-phenylethylamine are stirred into 352.4 g (1.7 moles) of racemic N-(2-ethyl-6-methylphenyl)-alanine in 3.61 g of diisopropyl ether. The salt begins to crystallise out after a short time. The bath is left to stand overnight, then the precipitate is isolated by filtration and washed with diisopropyl ether. The filter cake is recrystallised alternatively from ethyl acetate and acetonitrile until melting point and rotation are constant. Yield: 164.5 g of phenylethylamine salt with a melting point of 116°–118° C.; $[\alpha]^{20}_D = -19 + 1°$ (c = 1.01% in ethanol).

164 g (0.5 mole) of this salt are stirred for 5 minutes in 1.5 liters of ethyl acetate and 365 ml of 2N hydrochloric acid. The organic phase is separated, washed until neutral, dried over sodium sulfate and concentrated. Two recrystallisations from n-hexane give 84 g of S(−)-N-(2-ethyl-6-methylphenyl)-alanine. Melting point: 61°–63° C.; $[\alpha]^{20}_D = -12 + 1°$ (c = 0.92 % in ethanol).

(d) Preparation of S(−)-N-(1′-methyl-2′-hydroxyethyl)-2-ethyl-6-methylaniline

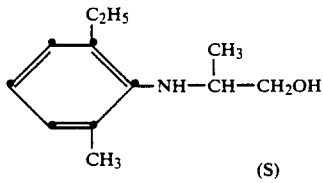

A solution of 124 g (0.64 mole) of S(−)-N-(2-ethyl-6-methylphenyl)-alanine in 1200 ml of anhydrous tetrahydrofuran is heated to reflux with the exclusion of moisture and while introducing dry N₂. Then 116 ml (1.16 moles) of borane-dimethyl sulfide complex are added very slowly dropwise, whereupon evolution of H₂ commences immediately. The reaction mixture is stirred under reflux for 20 hours and then cooled to 5° C. and methanol is added dropwise until the evolution of hydrogen ceases. The reaction mixture is concentrated in vacuo and the oily residue is taken up in ether and the ethereal solution is extracted portionwise with a total amount of 400 ml of 2N hydrochloric acid. The aqueous hydrochloric acid phases are combined, adjusted to pH 8 with concentrated sodium hydroxide solution while cooling with ice, and extracted with ether. The ethereal fraction is washed with water, dried and concentrated. The residue is distilled in a high vacuum, affording 104 g of S(−)-N-(1′-methyl-2′-hydroxyethyl)-2-ethyl-6-methylaniline with a boiling point of 103°–105° C. (10⁻³ mbar); $[\alpha]^{20}_D = 7 + 1°$ (c = 1.941 % in methanol).

(e) Preparation of aRS,1′S(+)-N-(1′-methyl-2-hydroxyethyl)-N-chloroacetyl-2-ethyl-6-methylaniline

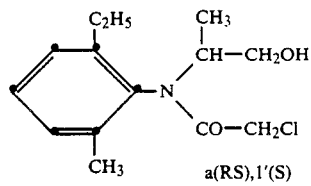

105 g (0.542 mole) of S(−)-N-(1′-methyl-2′-hydroxyethyl)-2-ethyl-6-methylaniline are mixed with 54.6 g (0.515 mole) of a carbonate in 800 ml of benzene, With efficient stirring, 41 ml (0.515 mole) of chloroacetyl chloride are slowly added dropwise at 15°–20° C. The reaction mixture is then stirred for 3 hours at room temperature and then filtered. The benzene filtrate is diluted with ethyl acetate and extracted in a separating funnel with water, 2N hydrochloric acid, 10% sodium bicarbonate solution and saturated sodium chloride solution. The organic phase is dried over sodium sulfate and concentrated in a rotary evaporator. The residual yellow oil is dried at 40° C. in a high vacuum and then further processed direct. Yield: 135 g; $[\alpha]^{20}_D = +12 \pm 1°$ (c = 1.166% in methanol).

(f) Preparation of aRS,1′S(−)-N-(1-methyl-2′-methoxyethyl)-N-chloroacetyl-2-ethyl-6-methylaniline

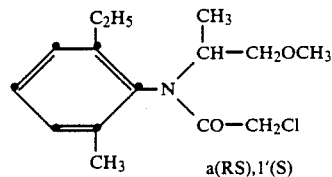

30.9 g (0.114 mole) of aRS,1′S(+)-N-(1-methyl-2′-hydroxyethyl)-N-chloroacetyl-2-ethyl-2-methyla niline, 23.8 ml (0.228 mole) of 2,2-dimethoxypropane and 3.5 g of p-toluenesulfonic acid are dissolved in 175 ml of absolute methanol and the solution is heated for 36 hours under reflux. After it has cooled to room temperature, the dark reaction mixture is concentrated and the residue is taken up in ethyl acetate. The ethyl acetate solution is extracted with 10% sodium bicarbonate solution and with water. The organic solution is dried over sodium sulfate and concentrated in vacuo and the residual oil is subjected to fractional distillation in a high vacuum.

Fraction I : 2.3 g ; b.p. : 124–126° C. (0.04 mbar) $[\alpha]^{20}_D = -8 \pm 1°$ (c = 2.946% in n-hexane Fraction II : 9.9 g: b.p. : 126–127° C. (0.04 mbar) $[\alpha]^{20}_D = -9 \pm 1°$ (c = 2.073% in n-hexane optical purity : 98 %.

Herbicidal activity

Example 2

The activity of the aRS,1′S(−)-isomer and the mixture of isomers of N-(1′-methyl-2′-methoxyethyl)-N-chloroacetyl-2-ethyl-6-methylaniline are compared in a herbicidal test in a greenhause. Both compounds are formulated to a 25 % emulsifiable concentrate of the following composition:
25 parts of active ingredient
5 parts of a mixture of nonylphenol polyoxyethylene and calcium dodecylbenzene sulfonate
15 parts of cyclohexanone
55 parts of xylene.

This concentrate is then diluted with water to the desired concentration.

The herbicidal activity is determined as follows:

Preemergence herbicidal activity (inhibition of germination)

Plant seeds are sown in pots with a diameter of 12–15 cm in a greenhouse. Immediately afterwards, the surface of the soil is treated with an aqueous dispersion of the test compounds, obtained from the emulsifiable concentrate. A range of concentrations is employed and the amount of active ingredient applied is in the range from 1 kg to 62.5 g per hectare. The pots are then kept in the greenhouse at a temperature of 22°–25° C. and at 50–70% relative humidity. The test is evaluated after 3 weeks and the results are expressed in accordance with the following rating:
1 = plants have not germinated or are totally withered
2–3 = very pronounced activity
4–6 = average activity
7–8 = slight activity
9 = no activity has untreated controls).

The results are reported in the following table. The term "Metolachlor" will be understood as meaning the unresolved racemic mixture of all possible diastereoisomers.

The far superior action against Cyperus, Echinochloa, Panicum, Sorghum, Portulaca and Amaranthus weeds is exerted even at low rates of application. As the racemate and the optically active compound have the same tolerance to cultivated plants above a rate of application of 1 kg/ha, the latter is far more selective and far safer when used for weed control. The problem weed *Cyperus esculentus*, for example, is effectively damaged by the optically active form even at a rate of application of 62.5 to 123 g/ha, whereas it is necessary to use almost 500 g of the racemate to obtain the same action.

Example 3

The use of the aRS,1'(−)-isomer of N-(1'-methyl-2'-methoxyethyl)-N-chloroacetyl-2-ethyl-6-methylaniline as a herbicide was also tested in the field and compared to that of the known mixture of isomers.

Test in Villimpenta near Mantova, Italy

A field was sown with corn of the variety "First" on April 20th and divided into lots. The lots were then sprayed individually with an emulsion of the compound to be tested in an amount corresponding to 1 and 1,5 kg/ha. Some lots were left untreated and served as control. The activity against the weeds was estimated by the occurrence of the leading weed Echinochloa crus galli (barnyard-grass). A first evaluation took place after 42 days on June 1st and another after 70 days on June 29th. The number of Echinochloa-plants was counted in each lot, averaged and compared with the average number that grew in the not-treated lots. The results are given below. No phytotoxicity was observed on the corn plants.

| Compound | application rate | % control of Echinocloa crus galli | |
|---|---|---|---|
| | | 42 days | 70 days |
| aRS,1'S(−)-isomer | 1 kg/ha | 100% | 90% |
| | 1,5 kg/ha | 100% | 94% |
| Metolachlor | 1 kg/ha | 70% | 80% |
| (racemic mixture) | 1,5 kg/ha | 90% | 85% |

Test in Fondanella/Spain

A field was sown with corn of the variety "P 3381" on May 14th and divided into lots. The lots were then individually sprayed on May 18th, with the substance to be tested in amounts corresponding to 1 or 1,5 kg/ha. Some lots were left untreated to serve as control. The activity was controlled by the occurrence of the leading weed Echinochloa crus galli (barnyard-grass) in each lot. The evaluation took place after 70 days on July 27th. The results are given below. There was no phytotoxic symptoms observed on the corn-plants.

| | Compound | | | | | | | | | |
|---|---|---|---|---|---|---|---|---|---|---|
| | "Metolachlor" (Racemate) | | | | | aRS,1'S(−) mixture of diastereoisomers | | | | |
| | Rate of application in kg/ha | | | | | | | | | |
| | 1000 | 500 | 250 | 125 | 62.5 | 1000 | 500 | 250 | 125 | 62.5 |
| maize | 8 | 9 | 9 | 9 | 9 | 9 | 9 | 9 | 9 | 9 |
| soybeans | 9 | 9 | 9 | 9 | 9 | 9 | 9 | 9 | 9 | 9 |
| sugar beet | 8 | 9 | 9 | 9 | 9 | 8 | 9 | 9 | 9 | 9 |
| cotton | 9 | 9 | 9 | 9 | 9 | 9 | 9 | 9 | 9 | 9 |
| Cyperus esculentus | 1 | 1 | 5 | 6 | 8 | 1 | 1 | 1 | 3 | 4 |
| Echinochloa crus galli | 1 | 1 | 2 | 3 | 5 | 1 | 1 | 1 | 2 | 3 |
| Panicum mil. | 1 | 2 | 4 | 4 | 8 | 1 | 1 | 2 | 4 | 9 |
| Pennisetum cland. | 1 | 2 | 4 | 8 | 9 | 1 | 3 | 3 | 6 | 8 |
| Setaria italica | 1 | 1 | 1 | 2 | 3 | 1 | 1 | 1 | 2 | 2 |
| Sorghum halepense | 1 | 3 | 6 | 6 | 9 | 1 | 1 | 3 | 8 | 9 |
| Sorghum sudan. | 2 | 2 | 8 | 9 | 9 | 1 | 1 | 3 | 5 | 8 |
| Lolium perenne | 1 | 2 | 3 | 4 | 7 | 2 | 2 | 2 | 3 | 5 |
| Bromus tectorum | 2 | 5 | 7 | 8 | 9 | 2 | 3 | 5 | 7 | 8 |
| Poa trivialis | 2 | 4 | 5 | 8 | 9 | 2 | 2 | 4 | 6 | 6 |
| Portulaca ol. | 1 | 5 | 9 | 9 | 9 | 1 | 1 | 6 | 9 | 9 |
| Amaranthus retr. | 1 | 1 | 3 | 6 | 8 | 1 | 1 | 1 | 2 | 4 |

| Compound tested | application rate | % control of *Echinochloa crus galli* |
|---|---|---|
| aRS,1'S(−)-isomer | 1 kg/ha | 97% |
| | 1,5 kg/ha | 99% |
| Metolachlor | 1 kg/ha | 88% |
| (isomer) | 1,5 kg/ha | 96% |

Test in Pawnee county, Kansas

A field was sown on June 21st with corn of the variety "Pioneer 3551". The field was then divided into lots and individual lots were sprayed the same day with an emulsion of the compound to be tested in amounts corresponding to 1 and 1,5 kg/ha. Some lots were left untreated to serve as control. The activity was controlled by the occurrence of the leeding weed Digitaria ascendis (crab-grass). The evaluation took place after 62 days in August 22nd and the results are as follows:

| Compound tested | Application rate | % control of *Digitaria ascendis* |
|---|---|---|
| aRS,1'S(−)-isomer | 1 kg/ha | 63% |
| | 1,5 kg/ha | 85% |
| "Metolachlor" | 1 kg/ha | 25% |
| (racemic mixture) | 1,5 kg/ha | 50% |

Test in Story county, Iowa

A field was sown with corn of the variety "G-4435" on June 24th, divided into lots and the individual lots were sprayed the same day with an emulsion of the compounds to be tested in amounts corresponding to 1,5 and 2 kg/ha. Certain lots were left untreated to serve as control. The activity was controlled by the occurrency of the leading weed Setaria faberii (foxtail). The evaluation took place after 81 days on Sept. 19. The results are given below:

| Compound tested | Application rate | control of *Setaria faberii* |
|---|---|---|
| aRS,1'S(−)-isomer | 1,5 kg/ha | 91% |
| | 2 kg/ha | 85% |
| "Metolachlor" | 1,5 kg/ha | 76% |
| (racemic mixture) | 2 kg/ha | 70% |

What is claimed is:

1. Optically active aRS,1'S(−)-N-(1'-methyl-2'-methoxyethyl)-N-chloroacetyl-2-ethyl-6-methylanili ne of the formula $$\text{(I)}$$

[structure: 2-ethyl-6-methylphenyl group attached to N, where N bears C*H(CH$_3$)—CH$_2$OCH$_3$ and COCH$_2$Cl substituents]

which is substantially free of the other isomers.

2. The optically active mixture of isomers aRS,1'S(−)-N-(1-methyl-2'-methoxyethyl)-N-chloroacetyl-2-ethyl-6-methylaniline according to claim 1 as an oil of 98% optical purity b.p. 124–127/0.04 mbar $[\alpha a]^{20}_D = -9 \pm 1°$ (c=2.073% in n-hexane).

3. A herbicidal composition which comprises as active ingredient a herbicidally effective amount of the optically active mixture of diastereoisomers of aRS,1'S(−)-N-(1'-methyl-2'-methoxyethyl)-N-chloroacetyl-2-ethyl-6-methylaniline, substantially free of other isomers, together with an inert adjuvant.

4. A method for controlling weeds in crops of cultivated plants selected from maize, cotton, soybeans and sugar beet, which comprises applying to said crops or the locus thereof a herbicidally effective amount of optically active aRS,1'S(−)-N-(1'-methyl-2'-methoxyethyl)-N-chloroacetyl-2-ethyl-6-methylaniline which is substantially free of the other isomers.

5. A method for controlling the wed Cyperus esculentus which method comprises applying to said weed or the locus thereof a herbicidally effective amount of aRS,1'S(−)-N-(1'-methyl-2-methoxyethyl)-N-chloroacetyl-2-ethyl-6-methylaniline, substantially free of the other isomers.

6. A method of claim 4 for controlling the weed Cyperus esculentus in crops of cultivated plants, which comprises applying to said plants or the area where the plants are grown a herbicidally effective amount of aRS,1'S(−)-N-(1'-methyl-2'-methoxyethyl)-N-chloroacetyl-2-ethyl-6 -methylaniline, substantially free of the other isomers.

* * * * *